United States Patent
Mueller (10) Patent No.: US 11,045,082 B2
(45) Date of Patent: Jun. 29, 2021

(54) CATHETER WITH OPTICAL SENSING

(71) Applicant: KONINKLIJKE PHILIPS N.V., Eindhoven (NL)

(72) Inventor: Manfred Mueller, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 473 days.

(21) Appl. No.: 15/749,636

(22) PCT Filed: Aug. 3, 2016

(86) PCT No.: PCT/EP2016/068475
§ 371 (c)(1),
(2) Date: Feb. 1, 2018

(87) PCT Pub. No.: WO2017/025390
PCT Pub. Date: Feb. 16, 2017

(65) Prior Publication Data
US 2018/0214017 A1    Aug. 2, 2018

(30) Foreign Application Priority Data

Aug. 13, 2015 (EP) .................................. 15180996

(51) Int. Cl.
*A61B 1/06* (2006.01)
*A61B 1/005* (2006.01)
(Continued)

(52) U.S. Cl.
CPC ........ *A61B 1/0615* (2013.01); *A61B 1/00177* (2013.01); *A61B 5/1076* (2013.01);
(Continued)

(58) Field of Classification Search
CPC .............. A61B 1/0615; A61B 1/00177; A61B 1/00078; A61B 1/00096; A61B 1/005;
(Continued)

(56) References Cited

U.S. PATENT DOCUMENTS 4,605,009 A * 8/1986 Pourcelot ........... A61B 1/00165
600/109
8,678,008 B2    3/2014 Rousseau et al.
(Continued)

FOREIGN PATENT DOCUMENTS

CN   201157608 Y   12/2008
JP   7184836 A    7/1995
(Continued)

OTHER PUBLICATIONS

Hoffstein, V. et al. (1991). The acoustic reflection technique for non-invasive assessment of upper airway area The European respiratory journal, 4(5), 602-11.

*Primary Examiner* — Timothy J Neal
*Assistant Examiner* — William B Chou (57) ABSTRACT

A catheter (12) has an image sensing system (S1-S5) for imaging the interior wall of a passageway in which the catheter is to be located. The catheter has a radial imaging system comprising a light source arrangement for generating a light output radially around the catheter and an image sensor for receiving the generally radial light after the light has been scattered back by the interior wall. The catheter is positioned within the passageway with a known position and orientation, for example a known angle with respect to the anterior-posterior plane along the length of the catheter, so that it is known where along the catheter length, and at which angular position around the catheter, it is close to the passageway wall. The light output has a different intensity at different radial directions and/or the catheter comprises a light transmission arrangement which gives rise to different transmission of the light output at different radial directions. These provide alternative measures to reduce the light received by the image sensor, thereby to prevent blooming in the captured image.

16 Claims, 4 Drawing Sheets

(51) Int. Cl.
| | |
|---|---|
| *A61B 1/267* | (2006.01) |
| *A61B 1/00* | (2006.01) |
| *A61B 5/107* | (2006.01) |
| *A61B 5/00* | (2006.01) |
| *A61M 25/00* | (2006.01) |
| *G02B 23/24* | (2006.01) |
| *G03B 15/05* | (2021.01) |
| *G01B 11/245* | (2006.01) |
| *G01B 11/25* | (2006.01) |
| *G03B 37/00* | (2021.01) |
| *A61M 25/01* | (2006.01) |

(52) U.S. Cl.
CPC .......... *A61B 5/1079* (2013.01); *A61B 5/4818* (2013.01); *A61B 5/6819* (2013.01); *A61M 25/0054* (2013.01); *G01B 11/245* (2013.01); *G01B 11/25* (2013.01); *G02B 23/2423* (2013.01); *G02B 23/2461* (2013.01); *G03B 15/05* (2013.01); *A61B 1/005* (2013.01); *A61B 1/00078* (2013.01); *A61B 1/00096* (2013.01); *A61B 1/267* (2013.01); *A61B 5/0084* (2013.01); *A61M 25/0023* (2013.01); *A61M 25/0138* (2013.01); *A61M 2230/00* (2013.01); *G03B 37/005* (2013.01)

(58) Field of Classification Search
CPC ..... A61B 1/267; A61B 5/1076; A61B 5/1079; A61B 5/4818; A61B 5/6819; A61B 5/0084; A61M 25/0054; A61M 25/0023; A61M 25/0138; A61M 2230/00; G01B 11/245; G01B 11/25; G03B 15/05; G03B 37/005; G02B 23/2423; G02B 23/2461
See application file for complete search history.

(56) References Cited

U.S. PATENT DOCUMENTS

| | | |
|---|---|---|
| 2002/0183623 A1 | 12/2002 | Tang et al. |
| 2003/0164952 A1 | 9/2003 | Deichmann et al. |
| 2004/0143254 A1 | 7/2004 | Vanney et al. |
| 2005/0081861 A1 | 4/2005 | Nasir |
| 2005/0096585 A1* | 5/2005 | Schon ................. A61M 1/3661 604/43 |
| 2007/0175482 A1 | 8/2007 | Kimmel et al. |
| 2007/0270717 A1 | 11/2007 | Tang et al. |
| 2008/0177139 A1* | 7/2008 | Courtney ............. A61B 5/0035 600/109 |
| 2008/0294002 A1 | 11/2008 | Xie |
| 2010/0016662 A1 | 1/2010 | Salsman et al. |
| 2010/0134607 A1 | 6/2010 | Ishihara |
| 2010/0313894 A1 | 12/2010 | Crumback et al. |
| 2011/0196200 A1 | 8/2011 | Glozman et al. |
| 2012/0265134 A1* | 10/2012 | Echarri ............. A61M 25/0032 604/95.05 |
| 2014/0148780 A1 | 5/2014 | Putz |
| 2015/0159998 A1 | 6/2015 | Altendorf |
| 2015/0201827 A1 | 7/2015 | Sidar |
| 2019/0374281 A1* | 12/2019 | Davies ............... A61B 18/1492 |

FOREIGN PATENT DOCUMENTS

| | | |
|---|---|---|
| JP | 10243920 A | 9/1998 |
| JP | 03342140 B2 | 11/2002 |
| JP | 2011206332 A | 10/2011 |
| KR | 2013034573 A | 4/2013 |
| WO | 1995001813 A1 | 1/1995 |
| WO | 02091913 A1 | 11/2002 |
| WO | 2010036541 A1 | 4/2010 |
| WO | 2015162186 A1 | 10/2015 |

\* cited by examiner

CATHETER WITH OPTICAL SENSING

CROSS-REFERENCE TO PRIOR APPLICATIONS

This application is the U.S. National Phase application under 35 U.S.C. § 371 of International Application Serial No. PCT/EP2016/068475, filed on 3 Aug. 2016, which claims the benefit of European Application Serial No. 15180996.9, filed on 13 Aug. 2015. These applications are hereby incorporated by reference herein.

FIELD OF THE INVENTION

The invention relates to a catheter with optical sensing, for example for measuring a passageway.

BACKGROUND OF THE INVENTION

A catheter camera for example comprises a radial imaging system in which a reflecting cone redirects light received (mainly) radially inwardly towards an essentially axial direction, for collection by an axially aligned camera. The received light is originally generated by a lighting system that projects a structured light pattern (e.g. a ring pattern) to the inside walls of the cavity in which the catheter is situated. A processor calculates the cross section of a passageway in which the catheter is located, for example by triangulation based on the image from the camera. An example of the use of such a catheter camera is for analysis of the upper airway, for determining the causes of obstructive sleep apnea.

Obstructive sleep apnea (OSA) is the most common kind of sleep apnea, affecting up to one in ten adults, and is characterized by the occurrence of pauses in breathing, or instances of shallow or infrequent breathing, during sleep. It is caused by blockage or obstruction of the oral cavity or upper airway, often due to loss of muscular tone during sleep. The incidence of OSA is often correlated with the onset of old age, obesity, or abuse of drugs or alcohol.

A range of therapies exist for treatment of OSA, the most common of which is positive airway pressure (PAP), in which a ventilator is used to deliver a stream of air through the airway at an elevated pressure, in order to hold open the airway. PAP is needed in more severe cases, where patients exhibit an apnea hypopnea index (AHI)>30. OSA patients may also suffer from daytime sleepiness and require therapy to prevent the development of comorbidities over the longer term. Mild-moderate OSA patients often have more difficulty adhering to PAP therapy because the disease burden is not as strong as in severe patients, and are therefore reluctant to submit to so invasive a therapy. In these cases, various alternative treatments exist, such as positional therapy, mandibular advancement (oral appliances), upper airway surgery and implantable devices.

In each of these therapies, however, it is important to understand which part(s) of the upper airway in particular is (are) causing obstruction, such that the therapy can be directed most effectively. This explains the interest in dynamic examinations of the upper airway preferably during natural sleep. One approach is to perform an examination of the airway non-invasively using acoustic reflectometry techniques. In such techniques, acoustic waves are propagated along the airway of the patient, by an emitter, via the mouth or nose, and reflections are listened for using a microphone adjacent to the emitter. It is possible, through algorithmic analysis of the detected reflections (see for example: Hoffstein, V., and J. J. Fredberg. "The acoustic reflection technique for non-invasive assessment of upper airway area." European Respiratory Journal 4.5 (1991): 602-611.), to determine an estimate of the cross-sectional area of the examined airway as a function of distance from the emitter. From this, narrowing of the airway at particular locations can be identified, and the specific positions therefore of airway obstructions ascertained.

Reflectometry techniques however suffer the disadvantage that the accuracy of cross-sectional area estimations declines with distance from the emitter. This is compounded by acoustic leakage and also patient movements during the measurement process, which both act to further compromise the accuracy of the obtained results. Furthermore, since the first obstruction encountered by a wave propagating along the airway causes reflection of much of the wave's initial intensity, reflections from subsequent portions of the airway are typically too weak in intensity to derive any accurate measurements. Hence it is typically only possible to accurately determine the location of the upper-most airway obstruction using these techniques. Finally the noise, size and the acoustic seal needed make the technique unfeasible for the examination of patients during natural sleep.

It is known instead to use endoscopic procedures, in particular procedures for inspecting or investigating the patency of the human upper airway. Using a standard flexible endoscope for airway examination, specific sites in the upper airway can be inspected for some time to see whether temporary obstructions occur. This however requires the endoscope to be moved from one spot to the other during an examination while the patient is asleep which is time-consuming and inconvenient for both the patient and the physician. For this reason endoscopic examination during natural sleep did not become part of common practice. An alternative version called Drug-Induced Sleep Endoscopy (DISE), which has become the standard care approach in some countries, involves bringing the patient to artificial sleep by means of sedative drugs. This is believed to cause collapses at sites that also participate in real sleep apneas and hypopneas. Also the sedation relieves the discomfort of endoscope travel. Acceptance of DISE remains limited, however, because the link between collapses in a sedated state and collapses during natural sleep remain unclear and may depend strongly on the depth of sedation and because of the costs and risks involved with sedation in general.

To inspect the upper airway at some discrete critical sites, it is also possible to use a catheter with multiple sensors; once the catheter has been inserted it can remain in the same position during a longer period without additional discomfort for the patient.

Image sensors can be used to obtain a measure of radial distance, for example if the image sensor is combined with an illumination element that projects a structured illumination pattern (e.g. a ring) on the inside of the airway, the captured image sensor information in respect of the ring image can be analyzed to derive distance information (e.g. by triangulation), and thereby enable the shape of the internal airway passage to be derived.

For example, an endoscope or catheter may have one or more light generating means capable of producing an outwardly directed ring (or radial plane) of light, such that when inserted into a tube-like airway, cross sectional contours of the airway may be illuminated for inspection by a camera.

One known means of providing such a light pattern is to direct collimated laser light from an optical fiber toward a deflecting cone whose angle is such as to deflect the incident light radially, for example at 90 degrees, from its surface in all directions around it. The effect is to create a 'ring' pattern of light projecting outwards from the cone, which may then be used to illuminate a circumferential section of an airway. In particular, there are two variations of this concept. In a first, the cone has a reflective outer surface, and is arranged with its tip facing in the direction of the oncoming light, such that light is reflected directly out from its surface. In a second, the cone is arranged with its base facing toward the oncoming light and the pitch arranged such that light incident from the optical fiber on the internal walls of the cone is reflected by total internal reflection in the direction of the opposing wall, through which it is transmitted, deflecting due to refraction as it does so into a path which is at 90 degrees to the initial incident light.

The reflected light is then captured by a camera. This may be achieved by positioning the camera with the inner wall being examined within the field of view, or else another reflecting cone may be used to redirect the reflected light back to an almost axial direction for capture by an axially aligned camera.

It is possible to create multiple ring patterns of light, at a series of spaced points along the airway. This can for example be achieved by means of providing multiple illumination units along the catheter, each with its own laser, optical fiber (optionally a GRIN lens) and cone.

When a catheter is deployed, gravity, the stiffness of the catheter material and the shape of airway will usually cause a catheter to stick closely to the anterior or the posterior airway wall at different depths of the airway.

This position of the catheter minimizes the distance between the sensor and the closest airway wall but maximizes the distance to the opposite airway wall. This typically leads to problems, in particular problems relating to the light intensity and the sensor range.

The light intensity that is reflected back towards the sensor decreases with the distance to the airway approximately as an inverse function with distance cubed. This is because the intensity of a ring light pattern is inversely proportional to distance (since it decreases in proportion with the circumference of the ring) while the light scattered back from the airway wall is diffusely scattered into all directions (approximately following Lambert's cosine law) leading to an intensity dependency proportional to the inverse of distance squared. For small distances between the sensor and the airway wall, the light intensity is very high, leading to blooming in the camera blurring the ring position. For large distances, the intensity is very low, making the ring difficult to see among the camera noise. The position of the catheter close to one airway wall thus maximizes the changes in wall distance, and therefore the light intensity differences.

Figure 3:
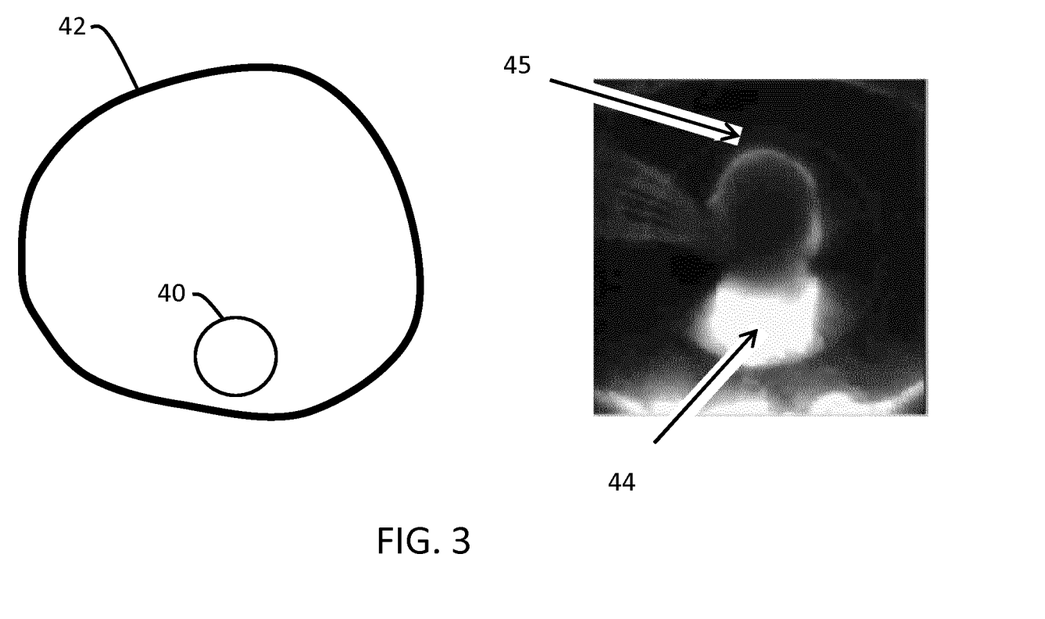
FIG. 3 shows a problem which arises due to non-central catheter positioning.

FIG. 3 shows in the left image a catheter 40 in cross section within the airway 42 and located to one side of the airway rather than in the middle. The right image shows a captured image in which there is blooming 44 at one part of the image and the image is dark in other parts of the image 55 so that the airway wall shape cannot be seen. The blooming also obscures the image of the airway wall shape. To capture a high quality image in such a situation, a camera with a high dynamic range (which is expensive) is needed to record the light pattern at all angles.

In addition the light dose that the airway closest to the sensor receives is unnecessarily high. This might cause unwanted side effects and compromise the safety of the patient by causing tissue damage. It is good practice to always minimize the radiation dose as much as possible.

With regard to the sensor range, it is difficult to optimize the optics part of a sensor to detect an airway wall both at very large distances and at very close distances. This is because a small camera typically has a very limited number of pixels. It is easy to optimize the sensor optics for short or for long airway wall distances but not for both.

There is therefore a need for a design which enables the imaging system to be able to tolerate non-central placement within the passageway being imaged, but without requiring highly complex imaging equipment.

SUMMARY OF THE INVENTION

The invention is defined by the claims.

According to an aspect of the invention, there is provided a catheter having an image sensing system for imaging the interior wall of a passageway in which the catheter is to be located, comprising:

a radial imaging system comprising a light source arrangement for generating a light output radially around the catheter and an image sensor for receiving the radial light output after reflection by the interior wall, wherein the catheter is adapted to be positioned within the passageway with predetermined position and orientation within the passageway along its length, and wherein the light output has a different intensity at different radial directions and/or the catheter comprises a light transmission arrangement which gives rise to different transmission of the light output to the image sensor for different radial directions, such that an envelope shape of the light output intensity distribution around the catheter or the light transmission function of the light transmission arrangement is non-circular.

By ensuring that the position of the catheter is known within the passageway, the optical system can then be designed so that the light received by the image sensor has a reduced intensity when blooming would otherwise occur. In this way, a higher quality image may be obtained without needing to increase the complexity of the image sensor. The position of the catheter is preferably known in that at a particular position along the length of the catheter, the position of the catheter cross section within the overall cross section of the passageway is approximately known, and also the angular orientation of the catheter is approximately known at that position. Thus, the catheter preferably has a known orientation relative to the closest passageway wall, i.e. a known orientation relative to the anterior-posterior plane. There is an asymmetric optical design adapted to the expected shape of the passageway and the expected orientation of the sensor with respect to the closest passageway wall.

The envelope shape of the light output intensity distribution around the catheter is the general shape around the catheter when following a light output intensity with a constant value. For example, for radial directions where the light output intensity is lower or there is more attenuation, the envelope shape will be nearer to the catheter. The general ring shape of illumination around the catheter is thus non-circular. The light output intensity may be a continuous ring or it may be discontinuous and then formed as a set of discrete points around a ring. In the latter case, it is this general ring shape which defines the envelope shape.

The light transmission function (to the optical sensor) is the amount of light transmission as a function of radial position. Thus, a non-circular light transmission function means the transmission is non-uniform around the circumference.

There are various ways to arrange that the catheter position is predetermined and therefore known in advance. It means that there is no need for feedback control of the envelope shape of the light intensity distribution or the transmission function. Instead, the catheter is designed to adopt a particular path (of position and orientation) within the passageway which is known in advance and the optical system (light source and image sensor and all optics between) is designed taking into account that known path.

In a first example, the catheter has a non-circular outer shape in cross section across the catheter length. This non circular shape means the catheter will have a preference to bending in certain directions. The non-circular shape is thus designed so that the inserted catheter follows a known path within a passageway which is itself of known general shape.

By way of example, the radius of curvature of the catheter outer shape, in cross section across the catheter length, may be greater at one angular position around the catheter compared to an opposite angular position around the catheter. The radius of curvature is designed to be greater at angular positions around the catheter where the catheter is to be in contact with the passageway wall. This gives rise to a generally squashed shape, i.e. wide and flat, with the flat parts against the passageway wall. A wide flat shape will bend preferentially around an axis parallel to the width direction.

The catheter may have a flat edge in its outer shape, in cross section across the catheter length, where the catheter is to be in contact with the passageway wall. The flat edge will preferentially stick to the airway wall, while the rounder parts are less likely to stick to the airway wall.

In all cases, the outer shape or angular orientation of the outer shape may vary along the catheter length. This means the catheter may be designed to follow a more complex path rather than simply bending around one curve. At different points along the length of the catheter, the catheter may make contact with a complex passageway at different angular positions. The angular orientation of the catheter shape or else the shape itself is thus varied to enable the flatter regions to be against the passageway wall.

In a second example, the bending properties of the catheter vary along the length of the catheter. This provides another way to control the way the catheter is steered into a known shape and location within the passageway. The catheter stiffness to bending in particular directions may for example vary along the length of the catheter.

These two approaches may be combined so that both shape and stiffness parameters are variables which together enable the catheter to adopt a desired shape when guided by the passageway, itself of generally known shape.

The light output has a different intensity at different radial directions and/or the catheter comprises a light transmission arrangement which gives rise to different transmission of the light output to the image sensor for different radial directions. These provide various options for controlling the light intensity reaching the image sensor from different directions. The intensity may be controlled at the light source (for example if different light source elements are responsible for light in different radial directions), or else the light intensity may be controlled as a function of radial direction before it is directed to the interior wall (for example by using an attenuation arrangement) or else the light intensity may be controlled as a function of radial direction when it is finally directed to the image sensor (for example by directing light to the image sensor differently for different directions from which the light is received from the interior wall). Controlling the light intensity involves changing the light transmission, whether by using attenuation or redirection of light away from the image sensor.

The light transmission may be controlled by varying an attenuation of an otherwise constant light source intensity.

The light output intensity may be least where the catheter is to be closest to the passageway wall. In this way, the output intensity is reduced where needed to avoid blooming, and it may be increased where there is a large distance to the passageway wall.

If a light attenuation arrangement is used, it may comprise electrical cables or optical fibers. In this way, existing components of the overall system may be used to provide a desired light blocking function, by designing their locations. This avoids the need for additional components. However, a dedicated light attenuation arrangement may of course be provided.

The light attenuation (as a function of radial position) may take place before the pattern is projected to the inner wall of the passageway or it may take place after reflection by the inner wall. The attenuation may involve absorption, or it may involve steering the light towards or away from specific directions. For example attenuation or reduced transmission insofar as the image sensor is concerned may be achieved be directing light away from the image sensor.

The terms "attenuation" and "transmission" should be understood accordingly.

The light source arrangement may comprise a light source inside the catheter, and optionally a collimator to collimate the light from the light source. The light source may direct light radially outwardly, or else it may direct light axially and a reflector may then be provided for redirecting the emitted light to form a ring of generally radially directed light around the catheter length.

Alternatively, the light source arrangement may comprise:
a light source outside the catheter;
an optical fiber which is adapted to transmit the light output from outside the catheter to the inside of the catheter and to emit the light in a direction centered parallel to the catheter elongate axis;
optionally a collimator to collimate light from the optical fiber; and
a reflector for redirecting the emitted light to form a ring of generally radially directed light around the catheter length.

This provides a compact design in which axially directed light is converted to radial light by a reflector, such as a reflecting cone.

The light source preferably comprises a laser or an LED.

The reflector may be non-axisymmetric thereby creating a non-uniform light intensity with respect to radial direction. In this way, a non-uniform radial light pattern is implemented by the reflector without requiring complex optical alterations to the light output.

The catheter may further comprise a second reflector for redirecting the radial light after reflection by the interior wall toward the image sensor. The second reflector may then be non-axisymmetric thereby creating a non-uniform camera sensitivity with respect to radial direction. Thus, the image sensor reflector is then used to implement the attenuation as a function of radial direction.

The catheter may be for use in determining the presence and location of obstructions in an upper airway, the catheter comprising a plurality of radial imaging systems along the length of the catheter. In this way, each radial imaging system is optimized for a particular one of the locations at which airway obstructions can be ascertained.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a catheter having an image sensing system for imaging the interior wall of a passageway in which the catheter is to be located. The catheter has a radial imaging system comprising a light source arrangement for generating a light output radially around the catheter and an image sensor for receiving the generally radial light after the light has been scattered back by the interior wall. The catheter is positioned within the passageway with a known position and orientation, for example a known angle with respect to the anterior-posterior plane along the length of the catheter, so that it is known where along the catheter length, and at which angular position around the catheter, it will be closest to the passageway wall. The light output has a different intensity at different radial directions and/or the catheter comprises a light attenuation arrangement which gives rise to different attenuation of the light output at different radial directions. These provide alternative measures to reduce the light received by the image sensor, thereby to prevent blooming in the captured image.

The invention may for example be used for imaging with a conduit. This may have non-medical applications for imaging non-living objects such as pipes, channels and tunnels as well as for medical imaging applications such as for imaging airway passages, intestinal passageway or capillaries or arteries.

Figure 1:
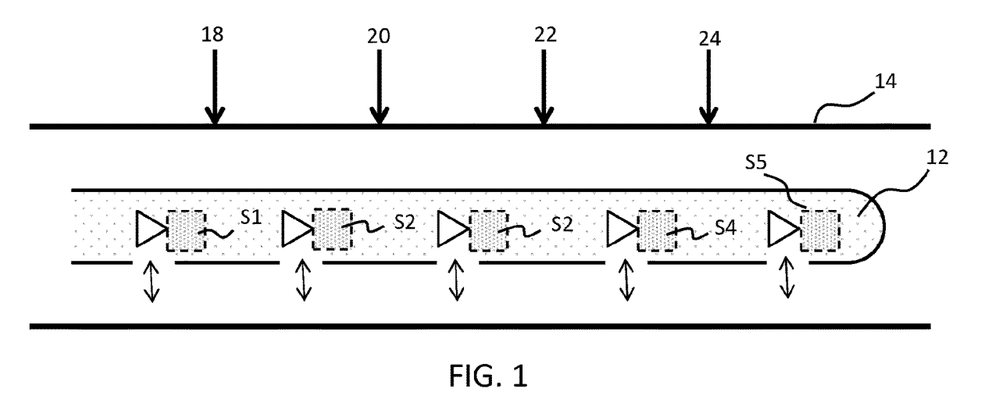
FIG. 1 shows a schematic illustration of a length section of an example catheter disposed inside an airway.

By way of illustration, FIG. 1 schematically depicts an example catheter 12 of known basic configuration, arranged within a stretch of an upper airway 14. Along the length of the airway are indicated four anatomical regions or features, labeled 18, 20, 22, and 24, these, by way of non-limiting example, representing the soft palate (velum), the oropharynx, the tongue base and the epiglottis respectively. Disposed within the airway 14 is the catheter 12, which comprises a series of optical sensors S1 to S5. They each comprise a laser light source for generating light generally axially, a first reflector for redirecting the light to include at least a component in the radial direction, a second reflector for redirecting reflected light from the side wall of the duct being investigated towards an image sensor for capturing an image of side wall of the duct being investigated. FIG. 1 shows schematically a space and therefore a radial distance between the catheter and the airway 14.

The optical arrangement is represented schematically in FIG. 1 as a single triangle.

Figure 2:
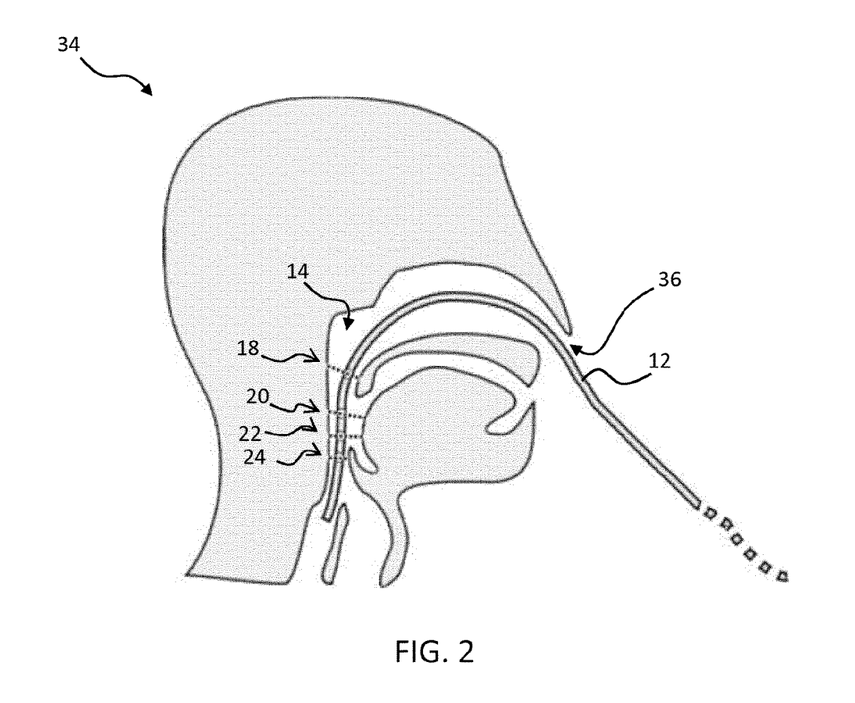
FIG. 2 shows a schematic illustration of an example catheter inserted into a patient's nasal cavity and upper airway.

For illustration, FIG. 2 schematically shows the catheter 12 disposed in the upper airway of a patient 34, having been inserted via the nostril 36 of the patient. The distal end of the sensor is anchored in the esophagus. The approximate positions of the four anatomical regions of FIG. 1 (velum 18, oropharynx 20, tongue base 22, and epiglottis 24) are indicated along the airway 14 of the patient 34.

This invention relates in particular to the issue of a non-central position of the catheter within the passageway and the effect this has on the radial light intensity captured by the imaging sensor.

The light source arrangement generates a radial ring of light emitting radially outwardly from the catheter to illuminate a ring shaped section of the wall of the upper airway 14. The ring may be continuous, but it may instead be formed as a set of discrete points generally following an annular path.

The radial projection may be entirely radial, i.e. at 90 degrees to the catheter axis, but it may be inclined at an acute angle to this perfectly radial direction. For compactness, for example to fit the optical system within a catheter, the light is routed axially along the catheter, and a reflection arrangement redirects the light to form the radial pattern.

As explained above, the distance between the catheter and airway wall influences the light intensity of the received light.

A first aspect of the invention involves ensuring the catheter has a known position within the passageway being imaged. One way to control this is to have control over the path followed by the catheter when it is inserted into the passageway.

Figure 4:
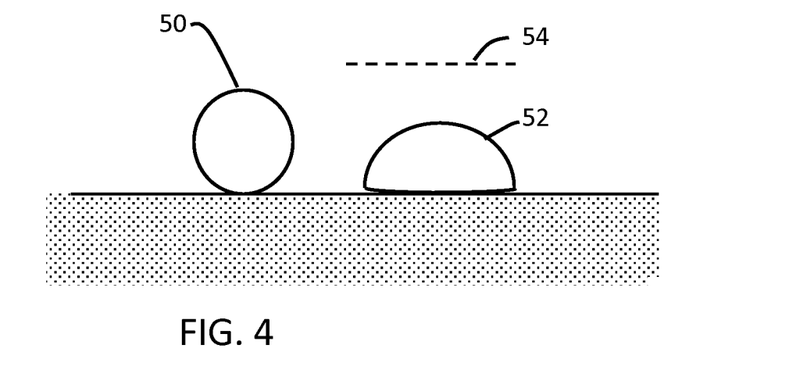
FIG. 4 shows how the catheter shape can influence the bending performance.

FIG. 4 shows how the catheter shape can influence the bending performance, which can then be used to control the shape and position adopted by the catheter. A circular cross section is shown as 50, and a cross section which is fattened is shown as 52. The outer shape 52 is non-circular in cross section across the catheter length. This non circular shape means the catheter will have a preference to bending in certain directions. In particular, it will preferentially bend around an axis 54 parallel to the width direction. In this way, the inserted catheter can be designed to follow a particular path to match the shape of a passageway which is itself of known general shape.

The radius of curvature of the catheter outer shape at the bottom is greater (i.e. there is a more gentle curve) than at the sides. This flatter bottom is where the catheter is to be in contact with the passageway wall. The outer shape is thus generally squashed. It may be an asymmetrical shape (i.e. with rotational order of symmetry equal to 1) but it may still have some symmetry, for example an ellipse which has a rotational order of symmetry of 2. The flatter bottom may be a completely flat edge The catheter thus has a smaller diameter in the height direction than in the width direction.

The most flattened side (the bottom in the example shown) is also particularly optimized to stick to the passageway wall.

When the catheter bends or flexes around the axis 54 the flat region will preferably orient itself towards the passageway wall. The catheter is entered into the passageway to support the correct alignment. In this way it is possible to predict the part of the sensor that will be closest to a passageway wall with a high degree of confidence.

It is also possible to obtain a similar behavior, without changing the geometric cross section of the catheter, but by adapting the mechanical properties for different orientations. This could be done for example by including stiff fibers in the catheter. In this way, the bending properties of the catheter vary along the length of the catheter. This provides another way to control the way the catheter is steered into a known shape and location within the passageway. The catheter stiffness to bending in particular directions may for example vary along the length of the catheter.

These two approaches may be combined so that both shape and stiffness parameters are variables which together enable the catheter to adopt a desired shape when guided by the passageway.

The approximate shape of the passageway, for example the upper airway, at a given depth is known. By controlling which side of the catheter is close to the airway, the light intensity can then be shaped according to the expected distance to the airway.

The light intensity can then be increased in directions where a large distance is expected to the airway wall, and the intensity can be decreased in directions where a small distance is expected.

Thus, in a second aspect, once the catheter position is known, there is control of the light pattern and/or the sensing optics to provide a non-rotationally symmetric function. In particular, when the light output intensity is controlled, the envelope shape of the light output intensity distribution around the catheter is non-circular. When the light intensity received by the image sensor is controlled by varying the light transmission with angle, the light transmission function is non-circular. The light dose and optical field of view around the sensor can then be optimized taking account of the known positioning.

Figure 5:
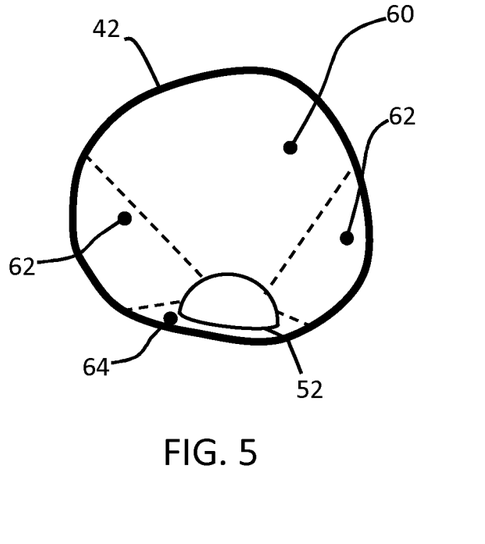
FIG. 5 shows a catheter with non-circular outer shape within a passageway.

FIG. 5 shows a catheter 52 with non-circular outer shape within a passageway 42. The intensity of the illumination pattern depends on the expected distance from the catheter. The light intensity is thus controlled to depend on the angular radial position around the catheter. For example, the intensity is highest in general region 60, lower in general region 62 and lowest in general region 64. The light intensity is not uniform in these regions, and they are only shown as three distinct regions for the purposes of explanation. In practice, there will be a function which relates the intensity to the angle around the catheter.

An asymmetric light pattern can be easily realized for example by adding different concentration of absorbers, or purposely misaligning the deflection cone which generates the radial light pattern from the center of the beam. In this way, the light pattern may be created by manipulating the output of the light source or the way it is reflected.

An alternative is to provide selective absorption of the light after it has been reflected for redirection radially. A dedicated light attenuation arrangement may be used for this purpose, but it may make use of existing parts of the device.

Figure 6:
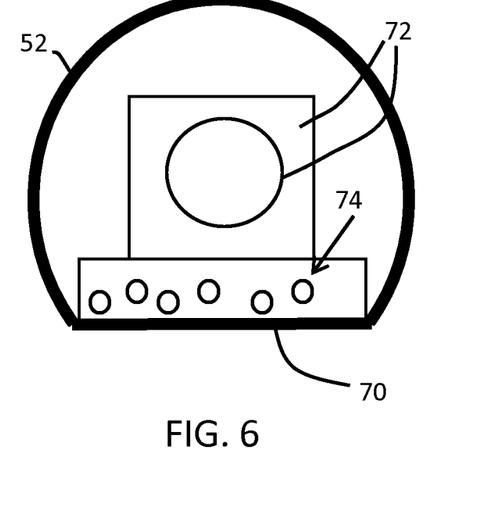
FIG. 6 shows how attenuation may be used to alter a radial light pattern.

FIG. 6 shows a non-circular catheter outer shape 52 (in cross section across the catheter length) with a flat edge 70 to be closest to the passageway wall. The catheter contains a camera and optical components 72 generally aligned along its central axis. There are various electrical cables or optical fibers 74 forming part of the device, and these are arranged at the flat side 70 to provide deliberate attenuation of the light from that area of the catheter outer wall. In this way, existing components of the overall system may be used to provide a desired light blocking function, by suitable selection of their locations. This avoids the need for additional components.

The various measures explained above for creating asymmetry may be oriented differently at different locations along the catheter length.

Figure 7:
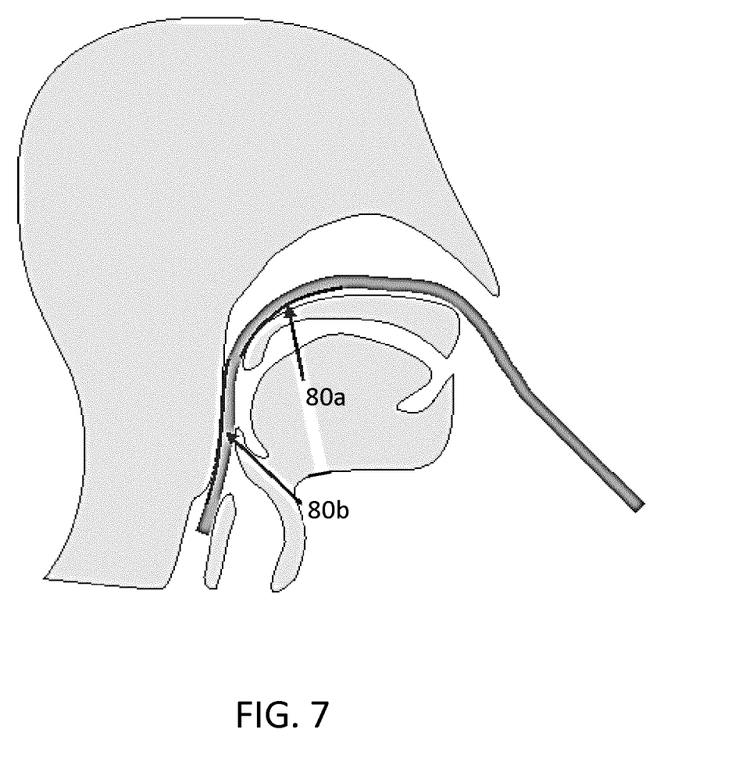
FIG. 7 shows how different orientations may be appropriate at different positions along the length of the catheter.

Like FIG. 2, FIG. 7 shows the catheter in use in the upper airway of a patient. In the manner explained above, the catheter is adapted along its length to match the orientation of the catheter to the airway wall.

For example, in FIG. 7 the catheter might prefer to stick close to the posterior walls at the level of the oropharynx until the epiglottis (location 80a) and stick close to the anterior airway wall at the velum level (location 80b). Therefore the catheter has the orientations of the flatter side change accordingly. Of course the other parameters could be adapted along the length of the catheter accordingly, such as the ring intensity, the orientation of cables or the catheter stiffness.

To provide an image sensor sensitivity which is dependent on radial direction, it is not only possible to adapt the intensity of the ring pattern according to the expected distance to the airway wall (as explained above), but it is also possible to adapt the distance range of the sensor. This can for example be implemented by using a non-rotational symmetric light collection cone in front of the camera, or by purposely misaligning the camera and the cone.

The resolution of such a sensor is typically limited by the number of pixels available in a small camera and by the field-of-view of the camera together with the light reflection cone. By using non-symmetric optics in front of the camera, the field of view of the camera changes depending on the radial direction. That means also that the pixels of the camera chip will be mapped differently depending on the radial direction. The asymmetry may be before the radial illumination pattern is formed (e.g. by design of the first reflector) or after it is formed but before it reaches the image sensor (e.g. by design of the second reflector) or both.

The invention may be applied to the catheter shown in FIG. 1.

The light source arrangement may comprise a light source such as a laser, an optical fiber which transmits the light output and emits the light in a direction centered parallel to the catheter elongate axis, and a first reflector for redirecting the emitted light to form a ring of generally radially directed light around the catheter length. It might also comprise a collimating element, which collimates the light from the fiber. This collimating element may be combined with the first reflector. This reflector may be designed to provide the asymmetric ring by its alignment or shape. For example, the reflector may be non-axisymmetric thereby creating a non-uniform light intensity with respect to radial direction. In this way, a non-uniform radial light pattern is implemented by the reflector without requiring complex optical alterations to the light output.

As mentioned above, an alternative is to implement the asymmetry using a second reflector which is for directing the light received from the passageway wall to the image sensor.

To illustrate the components mentioned above more clearly, FIG. 8 shows an illustrative example of a catheter 91 incorporating a radial illumination system as described above. The catheter 91 is encapsulated within a transparent capillary, and received a light output from a laser 92 which is outside the catheter, arranged to propagate generated laser light in an axial direction along an optical fiber 94. The laser is mounted at the end of the optical fiber. The optical fiber has a collimator and conical reflector 96 at its end 97.

Figure 8:
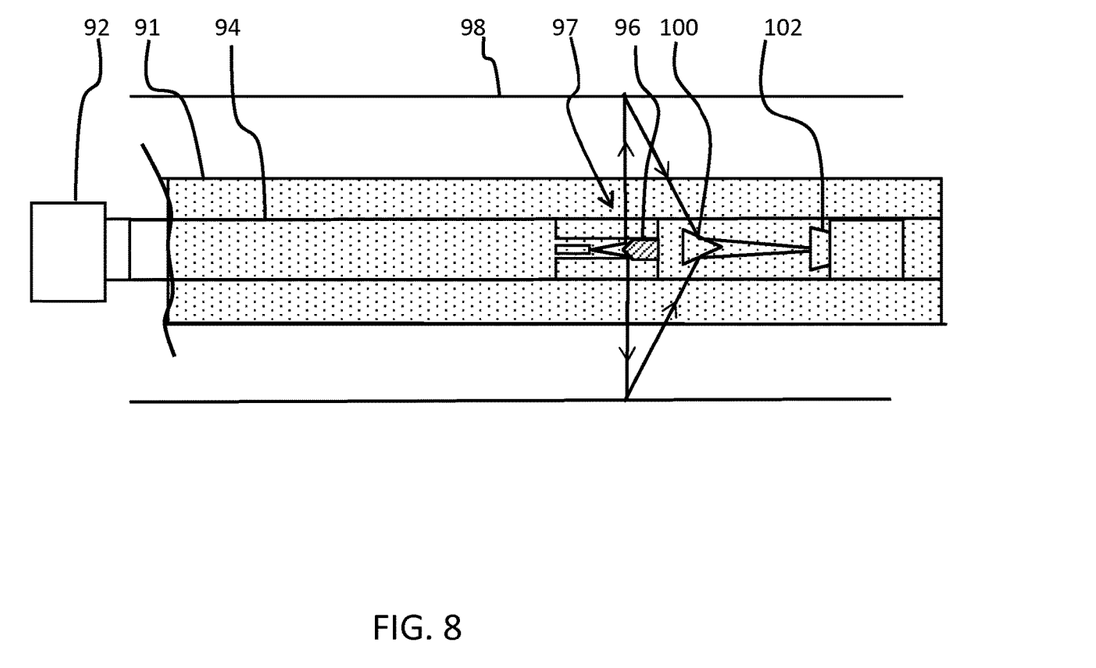
FIG. 8 shows a catheter design.

The reflector 96 may in some examples be designed to provide the required non-uniform light output intensity with respect to the radial direction as explained above.

The cross sectional shape of the catheter cannot be seen in FIG. 8. It may be non-circular as explained above.

The radial illumination system generates the radial light output, and after reflection by the channel in which the catheter is mounted (for example a patient airway 98), it is reflected by a cone reflector 100 towards an image sensor 102.

The catheter may comprise multiple imaging systems in series, whereas FIG. 8 shows only one such imaging system.

FIG. 8 also shows an external light source, whereas the light source may be inside the catheter. It may also for example comprise a ring of lighting elements which face outwardly (rather than axially), so that the reflector 96 is not needed. In this case, different lighting elements may have different intensity in order to vary the intensity with angular position around the catheter.

The catheter may be for use in determining the presence and location of obstructions in an upper airway, the catheter comprising a plurality of radial imaging systems along the length of the catheter. In this way, each radial imaging system is for a particular one of the locations at which airway obstructions can be ascertained.

As mentioned above, one application of particular interest is to improve the performance of an optical catheter sensor for measuring the upper airway patency in OSA patients during natural (or sedated) sleep; in this application a laser plane is created in the sensor module that is approximately perpendicular to the image sensor and cone axis and in the associated cross section in the upper airway a contour lights up. The sensor elements are contained in a capillary.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A catheter having an image sensing system for imaging the interior wall of a passageway in which the catheter is to be located, comprising:
    a radial imaging system comprising a light source arrangement for generating a light output radially around the catheter and an image sensor for receiving the radial light output after reflection by the interior wall,
    wherein the catheter is adapted to be positioned within the passageway with predetermined position and orientation within the passageway along its length, and
    wherein the light output has a different intensity at different radial directions and/or the catheter comprises a light transmission arrangement which gives rise to different transmission of the light output to the image sensor for different radial directions, such that an envelope shape of the light output intensity distribution around the catheter or a light transmission function of the light transmission arrangement around the catheter is non-circular,
    wherein the catheter has a noncircular outer shape in cross section across the catheter length that influences bending of the catheter in a known manner such that the catheter adopts a particular known path of position and orientation within the passageway due to the noncircular outer shape.

2. The catheter of claim 1, wherein the radius of curvature of the catheter outer shape, in cross section across the catheter length, is greater at one angular position around the catheter compared to an opposite angular position around the catheter.

3. The catheter of claim 2, wherein the catheter has a flat edge in its outer shape, in cross section across the catheter length, where the catheter is to be in contact or in close proximity with the passageway wall.

4. The catheter of claim 2, wherein the outer shape or angular orientation of the outer shape varies along the catheter length.

5. The catheter of claim 1, wherein the bending properties of the catheter vary along the length of the catheter.

6. The catheter of claim 5, wherein the catheter stiffness to bending in particular directions varies along the length of the catheter.

7. The catheter of claim 1, wherein the light output intensity is least where the catheter is to be closest to the passageway wall.

8. The catheter of claim 1, wherein the light transmission arrangement comprises electrical cables or optical fibers which provide attenuation.

9. The catheter of claim 1, wherein the light source arrangement comprises:
    a light source inside the catheter and optionally a collimator for collimating the light source output.

10. The catheter of claim 1, wherein the light source arrangement comprises:
    a light source outside the catheter;
    an optical fiber which is adapted to transmit the light output from the light source from outside the catheter to inside the catheter and to emit the light in a direction centered parallel to the catheter elongate axis;
    optionally a collimator for collimating the light from the optical fiber; and
    a reflector for redirecting the emitted light to form a ring of generally radially directed light around the catheter length.

11. The catheter of claim 10, wherein the reflector is non-axisymmetric thereby creating a non-uniform light intensity with respect to radial direction.

12. The catheter of claim 9, further comprising a second reflector for redirecting the radial light after reflection by the interior wall toward the image sensor.

13. The catheter of claim 12, wherein the second reflector is non-axisymmetric thereby creating a non-axisymmetric field-of view of the sensor with respect to radial direction.

14. The catheter of claim 1 for use in determining the presence and location of obstructions in an upper airway, wherein the catheter comprises a plurality of radial imaging systems along the length of the catheter.

15. The catheter of claim 1, wherein the intensity of the light at different radial directions is fixed.

16. A catheter having an image sensing system for imaging the interior wall of a passageway in which the catheter is to be located, comprising:
    a radial imaging system comprising a light source arrangement for generating a light output radially around the catheter and an image sensor for receiving the radial light output after reflection by the interior wall, wherein the catheter is adapted to be positioned within the passageway with predetermined position and orientation within the passageway along its length, and wherein the light output has a different intensity at different radial directions and/or the catheter comprises a light transmission arrangement which gives rise to different transmission of the light output to the image sensor for different radial directions, such that an envelope shape of the light output intensity distribution around the catheter or a light transmission function of the light transmission arrangement around the catheter is non-circular, wherein the catheter has bending properties that vary along the length of the catheter in a manner that influences bending of the catheter in a known manner such that the catheter adopts a particular known path of position and orientation within the passageway.

\* \* \* \* \*